(12) United States Patent
Robinson et al.

(10) Patent No.: US 10,292,735 B2
(45) Date of Patent: May 21, 2019

(54) ORTHOPEDIC IMPLANT FOR TREATMENT OF BONE DEFORMITIES

(71) Applicant: Bonfix Ltd., Jerusalem (IL)

(72) Inventors: Dror Robinson, M.P. Shemson (IL); Mark Shahar, Holon (IL); Nir Barkai, Kfar Saba (IL); Lew Schon, Pikesville, MD (US)

(73) Assignee: BONFIX LTD, Jerusalem (IL)

( * ) Notice: Subject to any disclaimer, the term of this patent is extended or adjusted under 35 U.S.C. 154(b) by 0 days.

(21) Appl. No.: 15/132,372

(22) Filed: Apr. 19, 2016

(65) Prior Publication Data
US 2016/0228152 A1 Aug. 11, 2016

Related U.S. Application Data

(63) Continuation of application No. 13/780,126, filed on Feb. 28, 2013, now Pat. No. 9,345,514, which is a
(Continued)

(51) Int. Cl.
*A61B 17/86* (2006.01)
*A61B 17/68* (2006.01)
(Continued)

(52) U.S. Cl.
CPC ........... *A61B 17/683* (2013.01); *A61B 17/68* (2013.01); *A61B 17/7291* (2013.01);
(Continued)

(58) Field of Classification Search
CPC ......... A61B 17/00; A61B 17/56; A61B 17/58; A61B 17/68; A61B 17/88; A61F 2/00;
(Continued)

(56) References Cited

U.S. PATENT DOCUMENTS

| 4,159,716 A | 7/1979 | Borders |
| 5,433,665 A | 7/1995 | Beaty et al. |

(Continued)

FOREIGN PATENT DOCUMENTS

| BE | 1 010 569 | 10/1998 |
| EP | 0760231 | 8/1996 |

(Continued)

OTHER PUBLICATIONS

Arnold et al. "Biomechanical in Vitro-Stability Testing on Human Specimens of a Locking Plate System Against Conventional Screw Fixation of a Proximal First Metatarsal lateral Displacement Osteotomy", The open Orthopedics Journal, 2012, 6, 133-139.
(Continued)

*Primary Examiner* — Nicholas J Plionis
*Assistant Examiner* — Steven J Cotroneo
(74) *Attorney, Agent, or Firm* — Pearl Cohen Zedek Latzer Baratz LLP; Mark S. Cohen

(57) ABSTRACT

An implantable orthopedic device. The device includes: a proximal anchor, configured to be implanted inside a first metatarsal; the anchor having a collar larger than the opening in a metatarsal in which the proximal anchor is implanted; the collar preventing cable to bone contact; a distal anchor, configured to be implanted inside a second metatarsal, adjacent to the first metatarsal; the distal anchor having a male thread, a nut threadable onto the male thread of the distal anchor, and a cord mechanically interconnecting the proximal and distal anchors. A shock absorber includes an elongate housing threadedly positioned within the anchor; the shock absorber accommodates a cord holder mechanically connected to the housing via a damping member, the cord holder is freely rotatable within the housing to prevent the cord from twist kinking when the housing is rotated to adjust a tension force.

17 Claims, 14 Drawing Sheets

Related U.S. Application Data continuation-in-part of application No. PCT/IB2011/053763, filed on Aug. 28, 2011.

(60) Provisional application No. 61/377,952, filed on Aug. 29, 2010.

(51) Int. Cl.
  *A61B 17/72* (2006.01)
  *A61B 17/84* (2006.01)
  *A61B 17/56* (2006.01)

(52) U.S. Cl.
  CPC .......... *A61B 17/842* (2013.01); *A61B 17/844* (2013.01); *A61B 2017/565* (2013.01); *A61B 2017/681* (2013.01)

(58) Field of Classification Search
  CPC ...... A61F 2/02; A61F 2/28; A61F 2/30; A61F 2/42
  See application file for complete search history.

(56) References Cited

U.S. PATENT DOCUMENTS

| | | | | |
|---|---|---|---|---|
| 5,507,812 | A * | 4/1996 | Moore | A61F 2/08 623/13.13 |
| 5,529,075 | A * | 6/1996 | Clark | A61B 17/68 128/898 |
| 5,575,819 | A | 11/1996 | Amis | |
| 5,800,543 | A | 9/1998 | McLeod et al. | |
| 5,941,885 | A | 8/1999 | Jackson | |
| 6,190,411 | B1 * | 2/2001 | Lo | A61F 2/0811 623/13.13 |
| 6,629,943 | B1 | 10/2003 | Schroder | |
| 7,625,395 | B2 * | 12/2009 | Muckter | A61B 17/8685 606/300 |
| 7,875,058 | B2 | 1/2011 | Holmes, Jr. | |
| 8,696,719 | B2 * | 4/2014 | Lofthouse | A61B 17/0401 606/104 |
| 8,808,374 | B2 * | 8/2014 | Eggli | A61B 17/0401 606/232 |
| 8,828,067 | B2 * | 9/2014 | Tipirneni | A61B 17/742 606/320 |
| 2003/0114857 | A1 | 6/2003 | Carchidi et al. | |
| 2003/0236555 | A1 | 12/2003 | Thornes | |
| 2005/0065533 | A1 * | 3/2005 | Magen | A61F 2/08 606/102 |
| 2005/0070906 | A1 * | 3/2005 | Clark | A61F 2/0805 606/60 |
| 2005/0149032 | A1 | 7/2005 | Vaughen et al. | |
| 2005/0240188 | A1 | 10/2005 | Chow et al. | |
| 2006/0074422 | A1 | 4/2006 | Story et al. | |
| 2006/0241608 | A1 | 10/2006 | Myerson et al. | |
| 2007/0010818 | A1 | 1/2007 | Stone et al. | |
| 2007/0161991 | A1 | 7/2007 | Altaric et al. | |
| 2007/0185489 | A1 | 8/2007 | Abdou | |
| 2008/0208252 | A1 * | 8/2008 | Holmes | A61B 17/0401 606/232 |
| 2008/0275563 | A1 | 11/2008 | Makower | |
| 2008/0288070 | A1 * | 11/2008 | Lo | A61B 17/0401 623/13.14 |
| 2009/0036893 | A1 * | 2/2009 | Kartalian | A61B 17/68 606/60 |
| 2009/0182336 | A1 | 7/2009 | Brenzel | |
| 2009/0287246 | A1 | 11/2009 | Cauldwell et al. | |
| 2010/0076504 | A1 * | 3/2010 | McNamara | A61B 17/0401 606/86 R |
| 2010/0082068 | A1 | 4/2010 | Graham | |
| 2010/0152752 | A1 | 6/2010 | Denove et al. | |
| 2010/0211071 | A1 * | 8/2010 | Lettmann | A61B 17/0401 606/60 |
| 2012/0130492 | A1 * | 5/2012 | Eggli | A61F 2/08 623/13.14 |

FOREIGN PATENT DOCUMENTS

| | | | |
|---|---|---|---|
| EP | 0998878 | 5/2000 | |
| WO | WO 2008/137487 A1 | 11/2008 | |
| WO | WO 2009/012001 | 1/2009 | |
| WO | WO 2009/018527 | 2/2009 | |
| WO | WO2009083047 * | 7/2009 | A61B 17/04 |
| WO | WO 2010/093696 | 8/2010 | |
| WO | WO 2010/106507 | 9/2010 | |
| WO | WO 2012/029008 | 3/2012 | |

OTHER PUBLICATIONS

International Search Report for PCT/IL2013/050362 dated Sep. 13, 2013.

Arthrex, Inc . "Comprehensive Solutions for Forefoot and Midfoot Surgery using the Mini TightRope® System." Arthrex Product Brochure (2008). Last accessed Apr. 16, 2014. <http://podiatrv.com/images/eZines/RI/0910/44/MiniTightRope.pdf>.

International Application PCT/IB2011/053763 Search Report dated Jan. 30, 2012.

International Application PCT/IB2011/051155 Search Report dated Sep. 20, 2010.

Artimplant AB. "Artelon Tissue Reinforcement", year 2011 (http://www.artimplant.com/patients/arlelon-tissue- reinforcement.html.

Depuy Mitek, Inc., "Fastin® RC Dual-Channeled Anchor", year 2007.

European Partial Search Report for Application No. 13181884.1 dated Jan. 8, 2014.

European Supplementary Search Report for Application No. 11821200.0 dated Aug. 26, 2014.

\* cited by examiner

ORTHOPEDIC IMPLANT FOR TREATMENT OF BONE DEFORMITIES

CROSS-REFERENCE TO RELATED APPLICATION

This application is a continuation of U.S. patent application Ser. No. 13/780,126, filed Feb. 28, 2013, which is a continuation in part of International Application No. PCT/IB2011/053763, filed Aug. 28, 2011, which claims priority to U.S. Provisional Patent Application 61/377,952, filed Aug. 29, 2010, now expired, both of which are incorporated by reference in their entireties.

FIELD OF THE INVENTION

The present invention relates generally to devices and methods for orthopedic surgical procedures, and specifically to implantable devices for treatment of deformities of the bones in the foot.

BACKGROUND OF THE INVENTION

"Hallux valgus" or "hallux abducto valgus" is a common disorder of the forefoot, which is associated with bunion deformity. The term refers to an abnormal slant of the big toe relative to the second toe. It is one of the most common pathologic conditions affecting the foot and toes.

Hallux valgus results from a medial deviation of the first metatarsal bone and lateral deviation and/or rotation of the big toe (hallux), with or without medial soft-tissue enlargement of the first metatarsal head (bunion). In normal feet, the angle between the first and second metatarsal bones (known as the Inter-Metatarsal Angle, or IMA) is typically in the range of 6-9°. In hallux valgus, this angle may increase to more than 12° in moderate cases and more than 16° in severe cases. Treatment of hallux valgus often includes surgical intervention to reduce the inter-metatarsal angle.

A number of surgical devices and techniques have been developed for reduction of the inter-metatarsal angle. For example, U.S. Patent Application Publication 2010/0152752, whose disclosure is incorporated herein by reference, describes a method and apparatus for bunion repair using a suture-passing K-wire. (A K-wire, or Kirschner wire, is a sharpened, smooth metal pin, widely used in orthopedic surgery, which is driven into the bone using a drill.) The K-wire is used to pass a suture through the first and second metatarsal bones. The first and second metatarsals are pushed together to correct the inter-metatarsal angle deformity, and the suture is tied in this position to hold anchor buttons against the bones. Arthrex, Inc. (Naples, Fla.) offers a commercial product of this sort, known as the Mini TightRope, which is also described in U.S. Pat. No. 7,875,058.

PCT International Publication WO 2009/018527 describes a fixation and alignment device for use in orthopedic surgery, for the correction of bone deformities. The device is part of an anchoring system that is said to be suitable for surgical repair of hallux valgus and other conditions. The system is used to anchor two or more sections of bone or other body parts and to align one section relative to another.

PCT International Publication WO 2010/093696 describes devices for treating hallux valgus using dynamic tensioning components or heat shrinkable components to urge two metatarsals together to treat a bone deformity. The dynamic tensioning component exhibits elasticity and has a tensioned state and an untensioned state. In the tensioned state, the component urges first and second anchors, attached to the first and second metatarsal bones, toward each other.

SUMMARY OF THE INVENTION

Embodiments of the present invention that are described herein below provide an implantable surgical device and a method of treatment of bone deformities, such as hallux abducto valgus.

There is therefore provided, in accordance with an embodiment of the present invention, an implantable device, comprising (a) a proximal anchor, configured to be implanted inside a first metatarsal (the first bone); said anchor having a tail collar which is larger than an opening in said metatarsal in which said proximal anchor is implanted; (b) a distal anchor, configured to be implanted inside (the second bone) e.g. a second metatarsal, adjacent to said first metatarsal; said distal anchor having a male thread; (c) a nut threadable onto said male thread of the distal anchor is possible; and (d) a cord mechanically interconnecting said proximal and distal anchors. At least one of said anchors is provided with a shock absorber.

It is a core purpose of the present invention is to provide said shock absorber comprising an elongate housing positioned within said anchor. The shock absorber accommodates a cord holder mechanically connected to said housing via a damping member, thereat said cord holder is can be freely rotatable within said housing to prevent said cord from twist kinking when said housing is rotated to adjust a tension force.

It is another object of the present invention to provide the damping member which is a spring.

It is another object of the present invention to provide a cable with changing amounts of tensions that acts as a ligament reconstruction support allowing guided tissue regeneration of inter-osseous ligament for example but not limited to the inter-metatarsal ligament. This cable may be coated with tissue growth enhancing material to simulate ligament reconstruction.

It is a further object of the present invention to provide the spring configured for operation under compression or extension.

It is a further object of the present invention to provide the at least one anchor provided with at least one tab deployable into a cortical area of a bone after implanting said anchor into.

In accordance with the present invention, a cord tension force is adjustable due to thread displacement of said shock absorber along said anchor.

It is a further object of the present invention to provide the said proximal anchor having a collar.

It is a further object of the present invention to provide the distal anchor having a male thread configured for threading a fixating nut at said thread to the rearward of said second metatarsal. However the distal anchor might also lack such a thread or have a female thread, It is a further object of the present invention to provide the distal anchor having a female thread configured for threading an extension rod for guiding said nut to be threaded onto said distal anchor.

It is a further object of the present invention to provide the shock absorber comprising an arcuate spring.

It is a further object of the present invention to provide the shock absorber comprising a telescopic element. It is a further object of the present invention to provide the shock absorber comprising a deformable sleeve that acts as a spring.

It is a further object of the present invention to provide the shock absorber comprising a deformable polymer bottleneck member.

In another embodiment of the present invention, the proximal or distal anchors or both might be inserted either oblique to or in parallel with the longitudinal axis of the bone or even perpendicular to it.

It is a further object of the present invention to provide a set for treating Hallux Abducto Valgus. The aforesaid set comprises (a) an implantable device further comprising: (i) a proximal anchor, configured to be implanted inside a first metatarsal; said anchor having a tail collar which is larger than an opening in said metatarsal in which said proximal anchor is implanted; (ii) a distal anchor, configured to be implanted inside a second metatarsal, adjacent to said first metatarsal; said distal anchor having a male thread; (iii) a nut threadable onto said male thread of the distal anchor; (iv) a cord mechanically interconnecting said proximal and distal anchors; at least one of said anchors provided with a shock absorber; (h) a K-wire drilling guide; and (c) a drilling device.

It is a further object of the present invention to provide the set comprising pliers configured for deploying said tab into said cortical area of a bone.

It is a further object of the present invention to provide the implantable device configured for an intramedullary insertion, without a male thread and nut threadable onto said male thread. It is a further object of the present invention to provide a method of surgically treating Hallux Abducto Valgus (HAV). The aforesaid method comprises the steps of: (a) providing a set treating HAV further comprising (i) an implantable device, comprising: (1) a proximal anchor, configured to be implanted inside a first metatarsal; said anchor having a tail collar which is larger than an opening in said metatarsal in which said proximal anchor is implanted; (2) a distal anchor, configured to be implanted inside a second metatarsal, adjacent to said first metatarsal; said distal anchor having a male thread; (3) a nut threadable onto said male thread of the distal anchor; (4) a cord mechanically interconnecting said proximal and distal anchors; at least one of said anchors provided with a shock absorber; (ii) a K-wire drilling guide; (iii) a drilling device; said shock absorber comprises an elongate housing threadly positioned within said anchor; said shock absorber accommodates a cord holder mechanically connected to said housing via a damping member, thereat said cord holder is freely rotatable within said housing to prevent said cord from twist kinking when said housing is rotated to adjust a tension force; (b) positioning said a K-wire drilling guide at the patient's foot such that said drilling device is directed for drilling first and second metatarsals; (c) making openings in said first and second metatarsals; (d) successively inserting said implantable device into obtained holes in said first and second metatarsals such that said proximal anchor is mechanically fixated in an opening in said first metatarsal while said distal anchor is shoved through an opening in said second metatarsal; (e) threading said nut at said male thread shoved through an opening in said second metatarsal to the rearward of said second metatarsal.

A further core purpose of the present invention is to provide the method comprising a step of damping mechanical effects during patient's ambulation by means of said shock absorber comprising an elongate housing threadly positioned within said anchor. The method comprises a step of adjusting a cord tension force by means of rotating said housing of said shock absorber such that said cord holder is freely rotatable within said housing to prevent said cord from twist kinking at said step of adjusting the cord tension force.

The present invention will be more fully understood from the following detailed description of the embodiments thereof, taken together with the drawings in which:

The present invention could be used for joining any two bones of the body including for example the tibia and fibula, the clavicle and the acromion, the clavicle and the coracoid process, the radius to ulna, or any of the carpal and tarsal bones.

The components could be implanted in an intramedullary location parallel or transverse or oblique to the bone.

A unique property of the variable tensioned cable is its ability to act as a tissue regenerating component supporting guided tissue regeneration of ligaments around the cable due to the threes on the cable as well as in some embodiments the specialized surface properties or layer enveloping the cable.

BRIEF DESCRIPTION OF TILE DRAWINGS

DETAILED DESCRIPTION OF EMBODIMENTS

Figure 1:
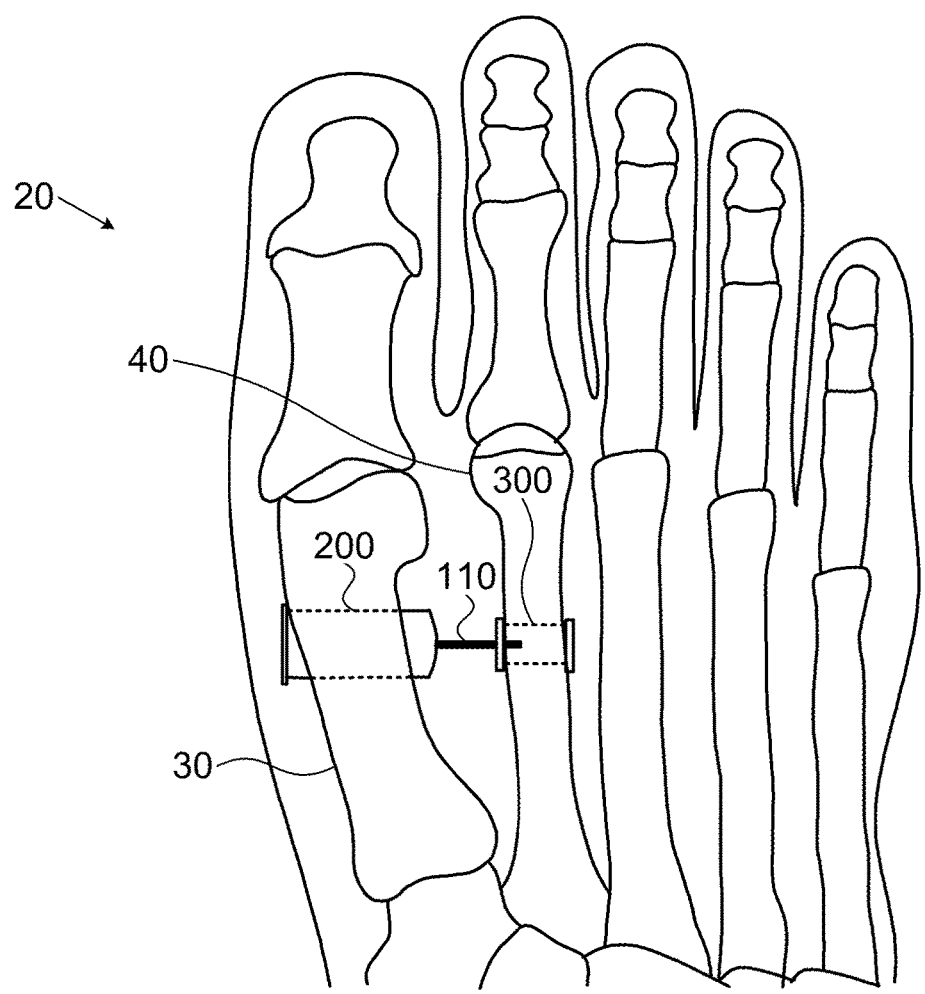
FIG. 1 is a schematic top view of the bones of a foot, in which a device for reducing inter-metatarsal angle has been implanted in accordance with an embodiment of the present invention.

Reference is now made to FIG. 1 presenting a schematic top view of the bones of a foot, in which a device 20 for reducing the inter-metatarsal angle has been implanted in accordance with an embodiment of the present invention. Device 20 comprises a first anchor 200, which is implanted in a first metatarsal bone 30, and a second anchor 300, implanted in a second metatarsal bone 40. The anchors are connected by a flexible or rigid cord 110, which extends between the anchors and thus between the two metatarsal bones 30 and 40). An adjustment mechanism, which is described in detail below and herein, enables the surgeon, after implantation of the anchors in the bones, to adjust the length of the cord extending between the first and second anchors. The surgeon can thus modify the inter-metatarsal distance, i.e. the IMA, meaning the angle between the respective axes of bones 30 and 40.

In the description that follows, it is assumed, for clarity of explanation, that the "proximal anchor" is implanted in the first metatarsal, while the "distal anchor" is implanted in the second metatarsal. In alternative embodiments, however, certain of the functions and features of the two anchors may be exchanged. Therefore, in the present patent application and in the claims, it should be understood that the terms "proximal" and "distal" are used arbitrarily in relation to the anchors and do not signify which anchor is to be implanted in which of the bones unless the specific context in which the terms are used indicates otherwise.

Although the devices and methods described herein relate specifically to the metatarsal bones and correction of conditions such as hallux valgus, the principles of the present invention may similarly be applied in other orthopedic applications, and particularly in treatments to modify the spacing between adjacent bones. For example, the devices described herein below may be modified for implantation in the metacarpal bones. Other examples of possible applications include closing of sternal osteotomies after open heart surgery; repair of rib fractures, allowing immediate immobilization of multiply fractured ribs; reduction of acromioclavicular dislocations; reduction of ulnar or fibular dislocated metacarpophalangeal or metatarsophalangeal joints, including treatment of Lisfranc fracture dislocation; treatment of ankle syndesmosis injury; dynamic linking of adjacent vertebrae, as an alternative to spinal fusion; treatment of flat foot; and treatment of hammer toe, treatment of scapho-lunate and radio-ulnar dislocations.

Figure 2:
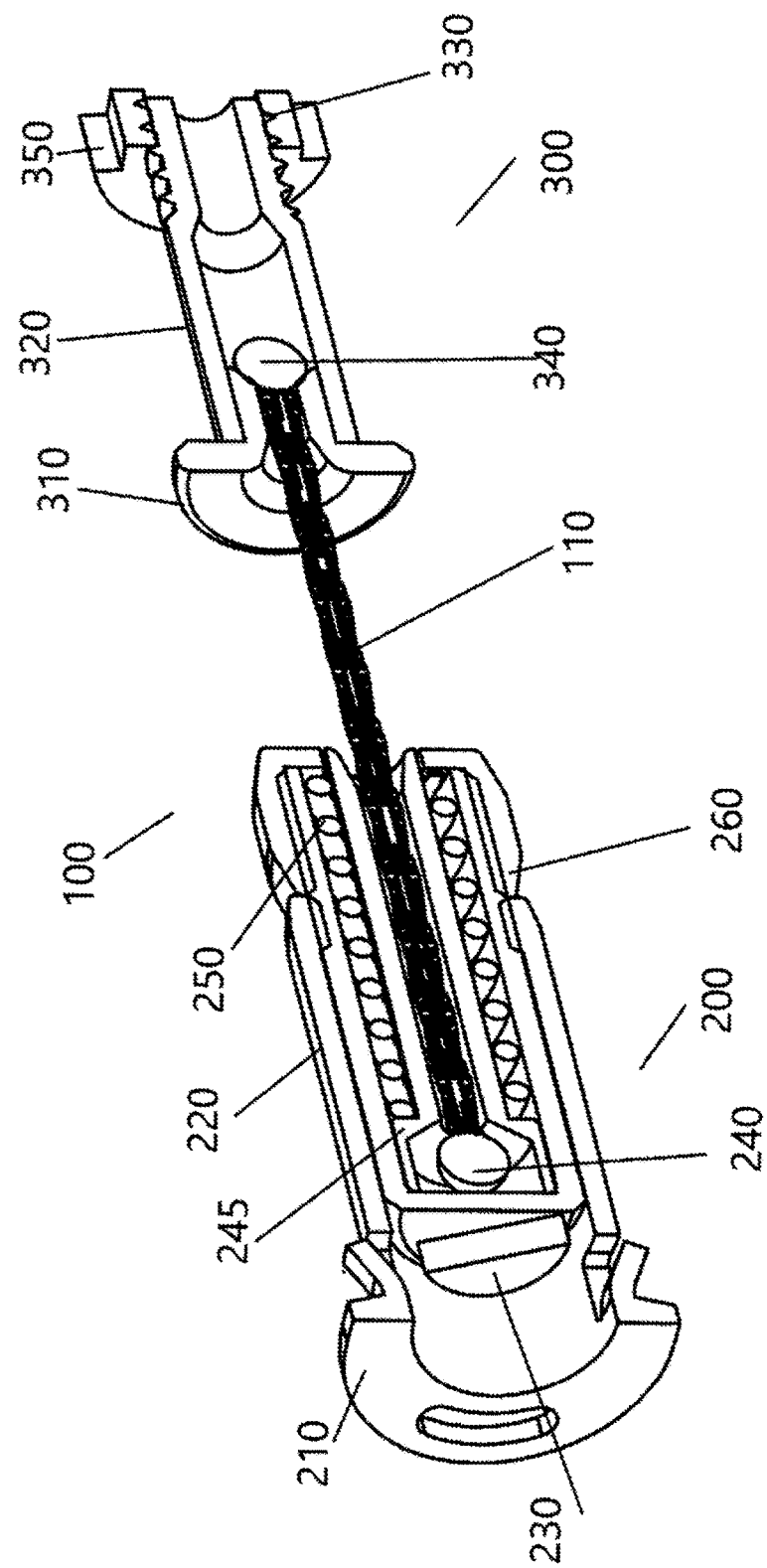
FIG. 2 is a schematic cross-sectional of an implantable device.

Reference is now made to FIG. 2 showing a cross-sectional view of an implantable device 100. The aforesaid device comprises a proximal anchor 200 configured to be implanted inside a first metatarsal and a distal anchor 300 configured to be implanted inside a second metatarsal. The proximal and distal anchors are interconnected by a cord 110. The proximal anchor 200 has (i) a collar 210 which is larger than an opening in the first metatarsal in which said proximal anchor is implanted; and (ii) a cylindrical portion 220. A shock absorber comprises an elongate housing 230 thready positioned within the anchor 200. A cord holder 245 is freely rotatable within said housing 230 to prevent said cord from twist kinking when said housing is rotated to adjust a tension force. The cord holder 245 have a passage there within with a bottleneck fastening a body 240 mechanically connected to the cord 110. A damping element (spring 250) is kinematically between the cord holder 245 and the housing 230 rigidly connected with the proximal anchor 200. A nut 260 is screwed onto the housing 230 and holds the spring 250 within the housing 230.

Similar to described, a body 340 connected to the cord 110 is fastened in the distal anchor 300. The aforesaid anchor 300 has a collar 310, a cylindrical portion 320 provided with a male thread 330. A nut 350 is designed for fixating the anchor 300 within the opening in the second metatarsal bone 40 (not shown).

It should be emphasized that, according to the present invention, the implant 100 consists of two anchors. The distal anchor 300 is of minor diameter in comparison with the proximal anchor 200. Openings in the first and second metatarsal bones 30 and 40 are made such that the distal anchor 300 freely passes through the first metatarsal and settles into the opening in the second metatarsal tightly. Respectively, the proximal anchor 200 into the opening in the first metatarsal tightly.

Anchors 200 and 300 are made from a rigid biocompatible material, such as 316LVM-type stainless steel or titanium alloy, with a cylindrical shape for insertion into cylindrical bores that are drilled in the bones. For example, anchor 200 may be 12 mm long and 6 mm in diameter, while anchor 300 is 11 mm long and 3 mm in diameter. Alternatively, other dimensions may be chosen depending, inter alia, on the dimensions and condition of the bones in which the anchors are to be implanted. Anchors 200 and 300 may be coated with a bone growth promoter, such as hydroxyapatite.

Cord 110 may comprise any flexible (though inelastic), biocompatible material of sufficient strength to withstand the forces exerted by and on the bones of the foot. The cord may comprise either a single strand or multiple strands of a suitable polymer or metal filament. For example, cord 110 may comprise a braided cable made from 316LVM-type stainless steel wire, with an overall diameter of about 0.5 mm.

The holder 245 also retains and compresses the spring 250. A threaded housing 230 controls the position of holder 245 and thus adjusts the degree of compression and the baseline force on spring 250. The threaded housing 230 has an outer thread, which travels along an inner thread in the anchor 200.

The spring 250 controls the tension in the cord 110. The spring typically comprises a flexible biocompatible material, such as stainless steelor cobalt chrome alloy. Alternatively, device 100 may comprise other sorts of mechanically-loaded elements that create mechanical resistance while deforming, such as a flexible polymer or viscoelastic material, a magnetic element applying mechanical force during movement, or a pneumatic or hydraulic element configured to resist geometrical movement.

The compression of the spring 250 can be adjusted by rotation of the threaded housing 230 (as described in greater detail herein below). Turning the threaded housing 230 clockwise (assuming the threaded housing to be right-handed) compresses the spring, creating a corresponding "zero-state tension" in cord 110. For example, the zero-state tension may be set to a value in the range between approximately 10 and 15 Newtons, although higher and lower values of tension may also be used, depending on clinical conditions.

The longitudinal position of holder 245 within anchor 200 is controlled by an adjustment mechanism comprising screw 44, which travels along internal thread 46 inside the anchor. For example, turning screw 44 counterclockwise (assuming thread 46 to be right-handed) causes holder 40 to shift longitudinally in the proximal direction, thus drawing cord 30 into anchor 22. In this manner, the length of the cord extending between the anchors is reduced, and the inter-metatarsal angle is reduced accordingly. Alternatively, screw 44 may be turned clockwise to play out the cord and thus reduce the force exerted between the metatarsal bones.

The implantable device is, for example, configured for an intramedullary insertion and provided without said male thread and a nut threadable onto said male thread is also in the scope of the present invention.

Figure 3:
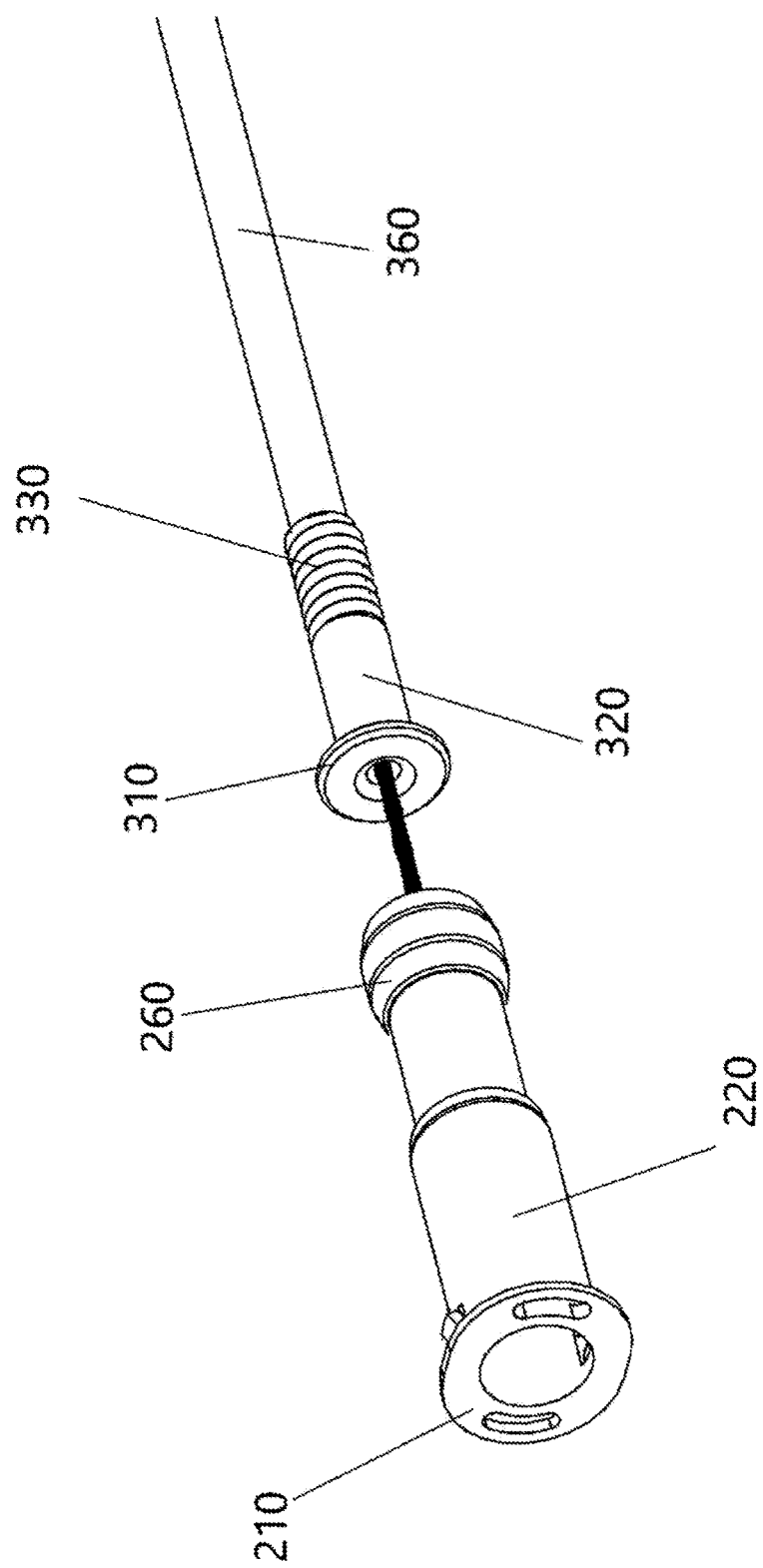
FIG. 3 is a schematic view of the device provided with an extension shaft.
Figure 4:
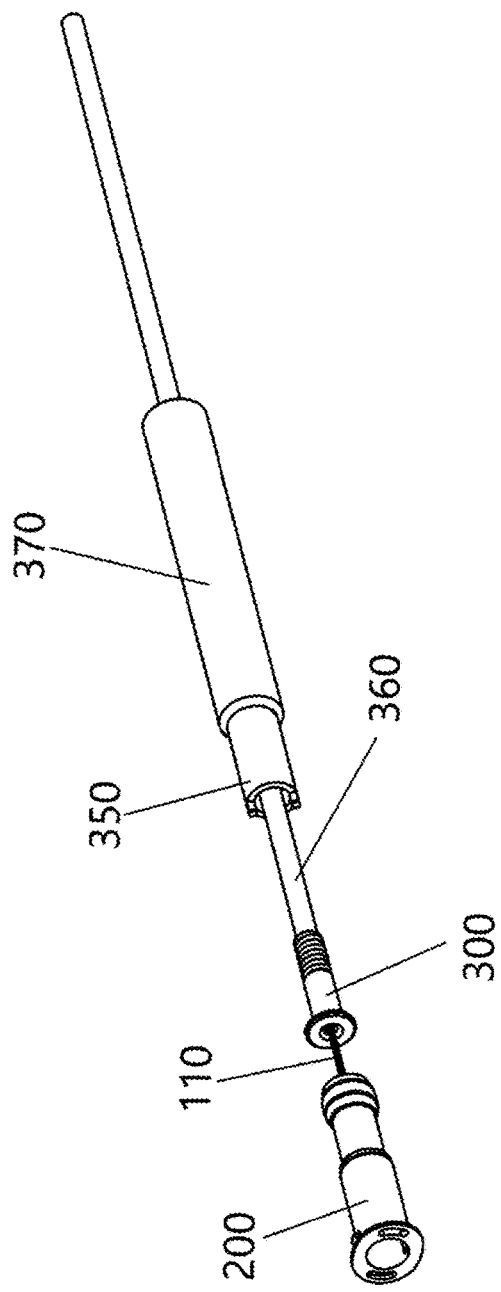
FIG. 4 is a schematic view of the device provided with a nut and a locking tool.
Figure 5:
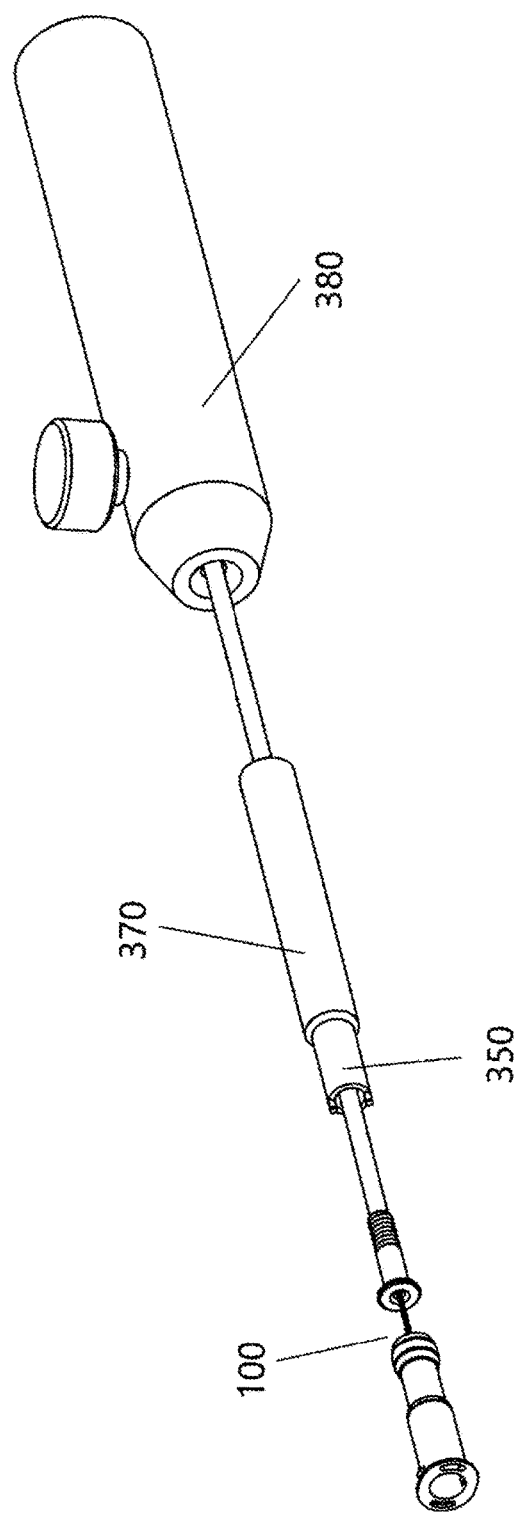
FIG. 5 is a schematic view of the device provided with a handle.
Figure 6:
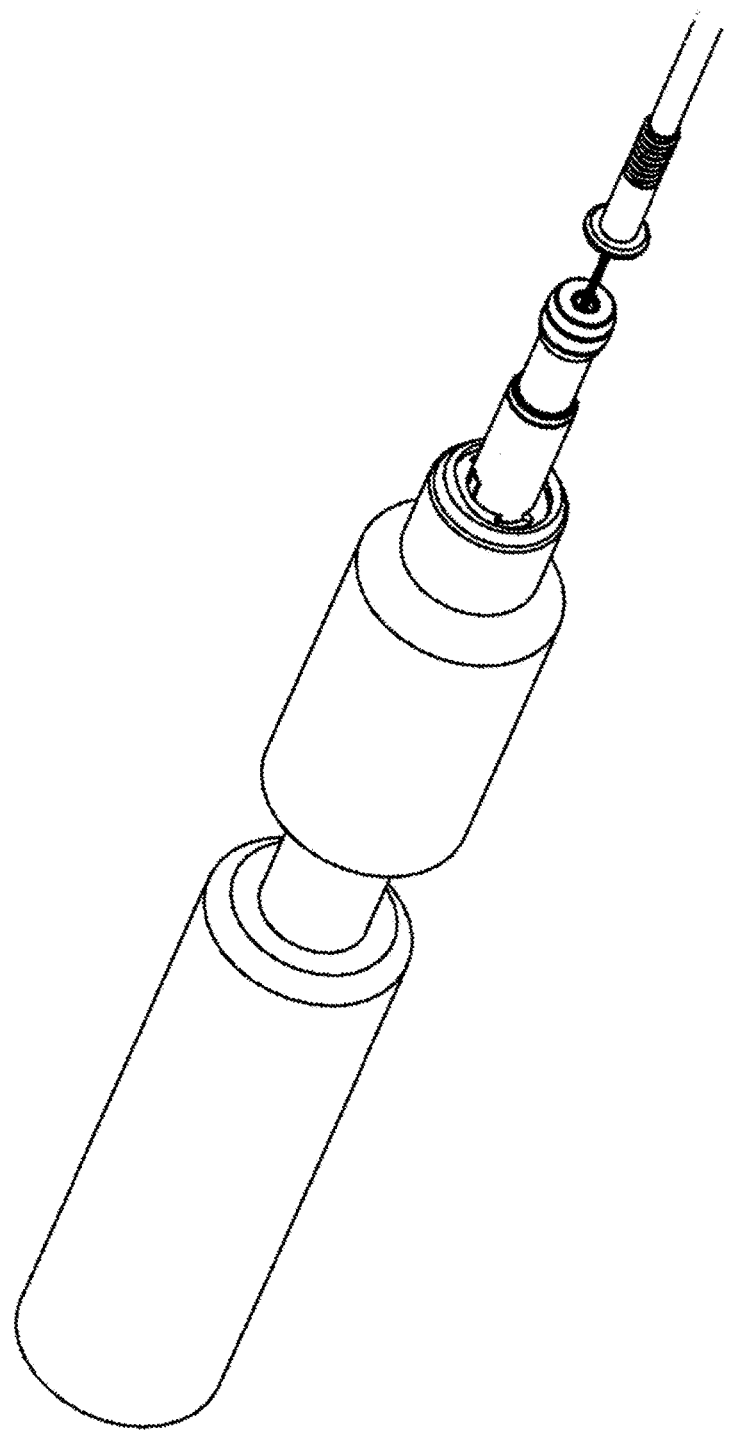
FIG. 6 is a schematic view of the device provided with an adjusting tool fitted into the device.

Reference is now made to FIGS. 3-7, presenting specific technologic tools. FIG. 3 shows an extension shaft 360 which is screwable into a cylindrical portion 320 of the distal anchor. The extension shaft 360 is used as guide for mounting the nut 350 onto the cylindrical portion 320. Specifically, FIG. 4 illustrates sliding the nut 350 and a locking tool 370 along the extension shaft 360. In FIG. 5, a handle 380 is used for threading the nut 350 for its fixation at the distal anchor. The nut 350 secures the device 100 at the distal side. After threading the nut 350, locking tool 370 held by the handle 380 are removed. FIG. 6 schematically presents a step of adjusting a cord tension force. Practically, a tool configured for rotating the housing 230 (not shown) held by a handle 280 longitudinally displaces the housing 230 within the anchor 200 (not shown).

Figure 7:
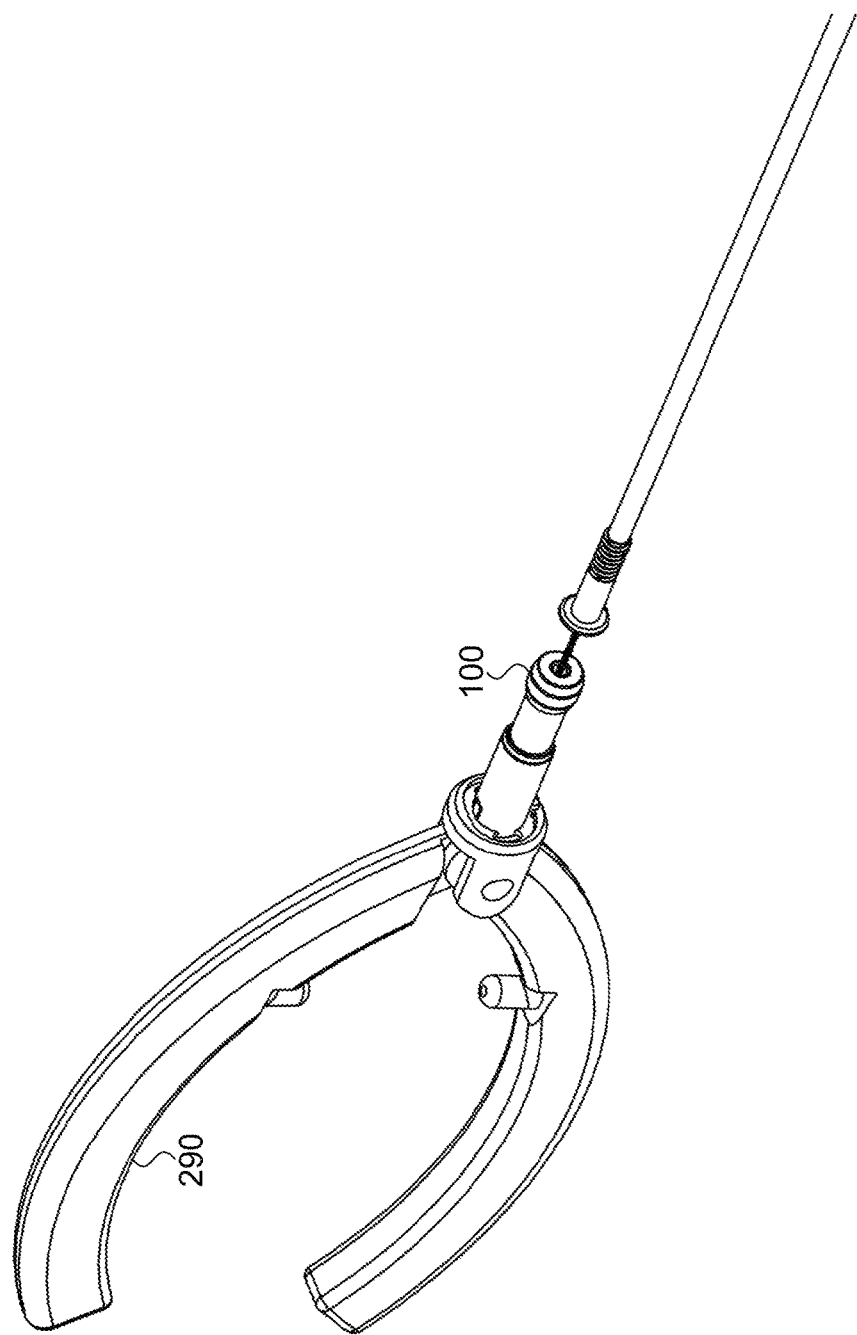
FIG. 7 is a schematic view of the device provided with locking pliers.

FIG. 7 shows a tool 290 designed for deploying at least one tab into a cortical area of a bone after implanting said anchor into.

Figure 8:
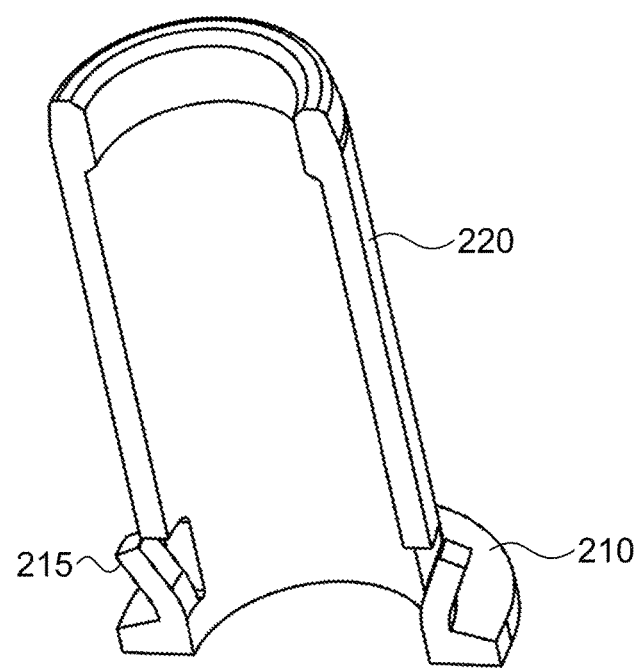
FIG. 8 is a phantom view of a housing of a proximal anchor.

Reference is now made to FIG. 8, schematically presenting a phantom view of a housing of a proximal anchor. A tab 215 is bent (deployed) into the cortical area of a bone (not shown) after implanting said anchor.

Figure 9:
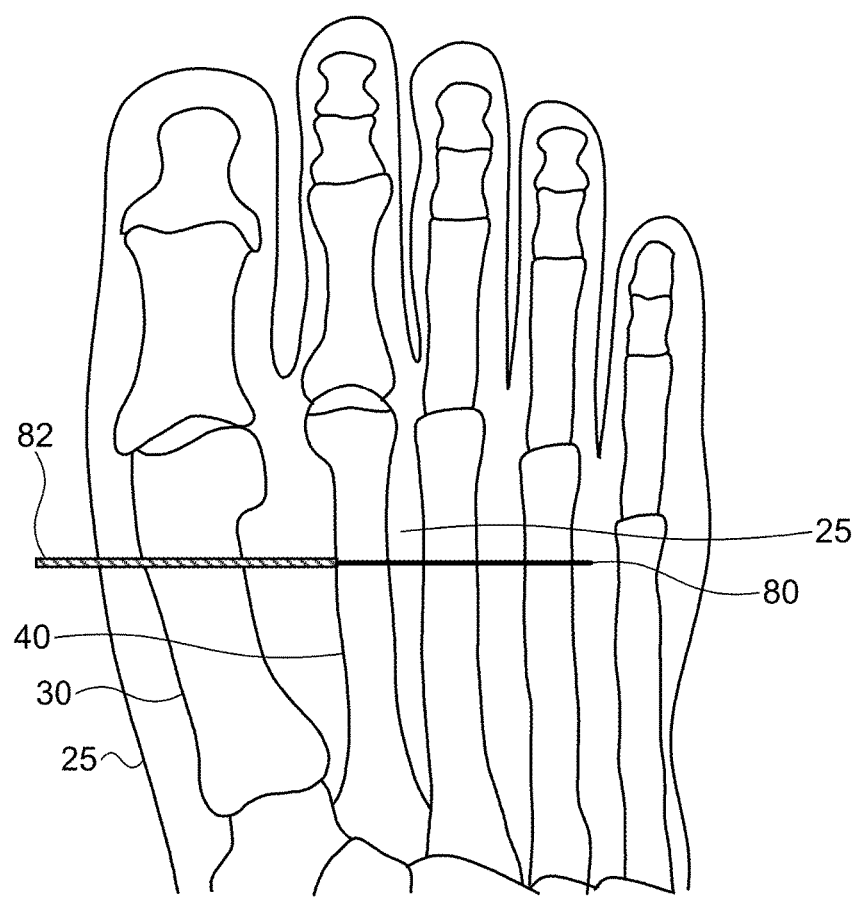
FIG. 9 is a scheme illustrating a preparatory stage in a procedure for device implantation.
Figure 10:
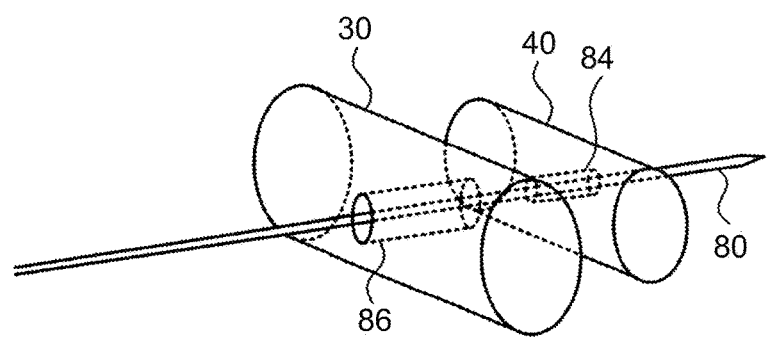
FIGS. 10-13 are schematic, pictorial views of the first and second metatarsal bones showing successive stages of the surgical procedure.

FIG. 9 is a schematic top view of a foot showing a preparatory stage in a procedure for treatment of hallux valgus using device 100, in accordance with an embodiment of the present invention. As an initial step, the surgeon may make incisions at locations 25, i.e., at the medial end of the first metatarsal and the lateral end of the second metatarsal. The surgeon may then remove the medial eminence (excess tissue) from the bunion on first metatarsal bone 30 and may cut the adductor tendon away from the first metatarsal bone so that the first and second metatarsal bones can be brought closer together. These surgical steps are known in the art and are outside the scope of the present patent application.

The surgeon first reduces the distance between first and second metatarsal bones 30, 40 by applying force on the first metatarsal toward the second metatarsal, either by hand or using a suitable tool, such as a special-purpose clamp (not shown). Following this step, the surgeon percutaneously drills a K-wire 80 through first and second metatarsal bones 30 and 40 using a drill guide (not shown). The K-Wire diameter may be, for example, 1.1 mm. The surgeon then drills through bones 30 and 40 using a cannulated drill 82 over K-wire 80. In the present example, drill 82 has a diameter of 2.8 mm, slightly smaller than the outer diameter of anchor 300.

FIGS. 10-13 are schematic, pictorial representations of bones 30 and 40, showing successive stages in the surgical procedure, in accordance with an embodiment of the present invention. In FIG. 8, a 2.8 mm bore 84 has been drilled in second metatarsal bone 28. The surgeon then uses a larger drill, for example, 6 mm in diameter, to create a larger bore 86 in first metatarsal bone 30, K-wire 80 remains in the bores at this stage.

To aid in insertion of anchors 200 and 300, a tube 360, such as a plastic pipe or cannulated metal tube (made from 316-type stainless steel, for example), is used as an surgical aid. Tube 360 may have a handle 380 attached to facilitate manipulation by the surgeon.

Figure 11:
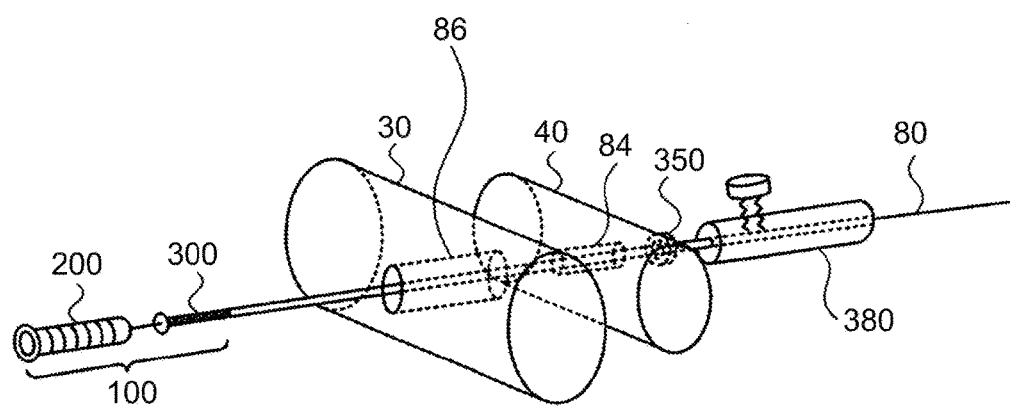

As shown in FIG. 11, the surgeon slides tube 360 over K-wire 80 through bores 84 and 86. Then, the distal end of tube 360 is attached to anchor 300. Next, the surgeon pulls the K-wire out of the bores in the distal direction. The surgeon then pulls the tube in the distal direction to draw anchors 300 and 200 through bore 86 in turn, until the anchors are inserted fully into bores 84 and 86, respectively.

In an alternative embodiment, tube 360 may be pre-attached to implant 300 at the factory by laser welding, for example. In this case, handle 380 may be pulled over the distal end tube 360 from bore 86 to 84 and secured to the tube by a screw knob 380.

Figure 12:
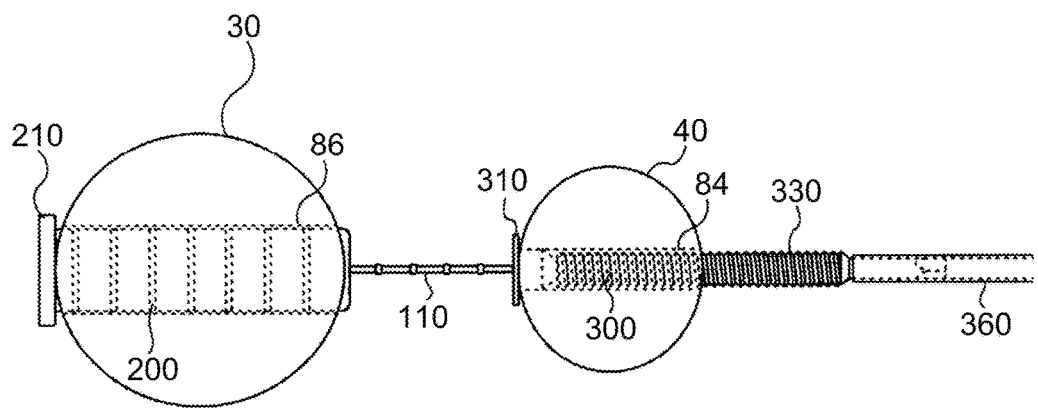
Figure 13:
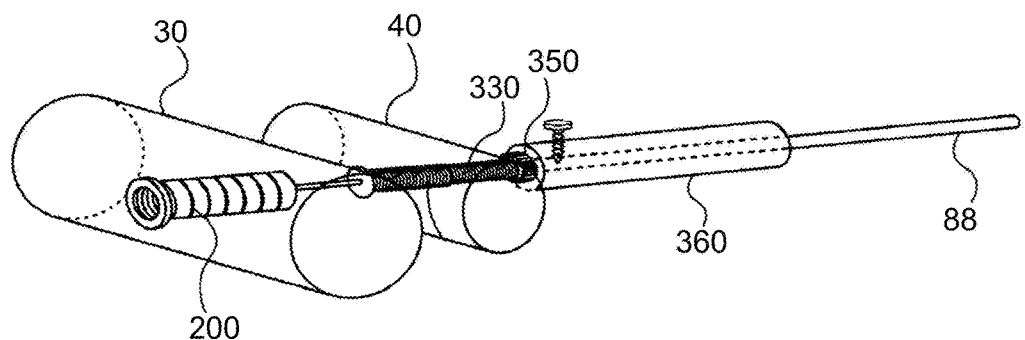

The final positions of the anchors 200 and 300 in bores 86 and 84, respectively, are shown in FIG. 12. Collars 210 and 310 engage the respective surfaces of bones 30 and 40 on the proximal side, while thread 330 and tube 360 protrude outward from bore 84 on the distal side. To secure anchor 300 in place, the surgeon loosens tool 89 from tube 360 and slides nut 350, which resides on tool 89, over tube 350, as shown in FIG. 13. The surgeon then tightens the nut over thread 330 using tool 89 to engage the distal side of bone 40.

Final adjustment of the cord tension force is performed by the special tool 270 (FIG. 6) which is configured for rotating the housing 230 (see FIG. 1) threadly positioned within the proximal anchor 200. The aforesaid anchor 200 is additionally fixated within the first metatarsal by deploying at least one tab into a cortical area of the bone (see FIG. 8).

The cable might be coated with tissue growth promoters such as collagen or growth supporting polymers or a specially roughened surface to promote tissue attachment or alternatively a smooth surface preventing tissue attachment as needed per specific indication.

The tension of the cable acts as a tissue guiding element allowing regeneration of tissue along the cable and establishing a force-sharing function of the cable.

Figure 14:
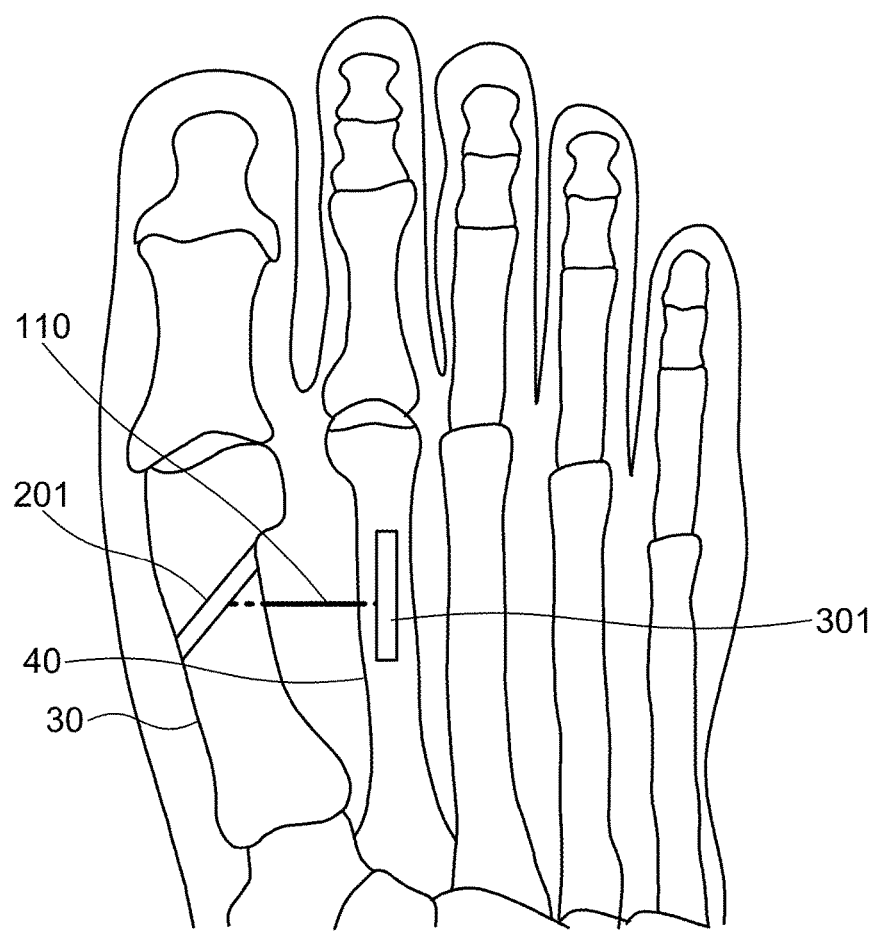
FIG. 14 is a schematic illustration of an alternative arrangement of the implantable device.

Reference is now made to FIG. 14, showing an alternative embodiment of the present invention. Numerals 201 and 301 refer to locations and orientations where the proximal and distal anchors can be implanted, respectively. In accordance with the instant embodiments, the anchors can be implanted within the bones inclined or longitudinally relative to the bones.

Figure 15:
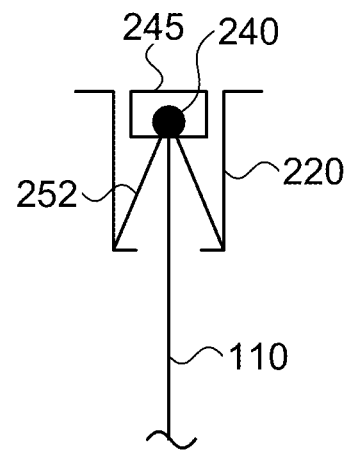
FIGS. 15 and 16 are schematic views of alternative embodiments of the shock absorbing mechanism.

Reference is now made to FIG. 15, presenting an alternative embodiment of the shock absorbing mechanism comprising an arcuate spring 252 made by press forming. The spring 252 is elastically deformable as affected by the member 250 puled by the cord 110. The spring 252 dampens oscillations in the cord tension.

Figure 16:
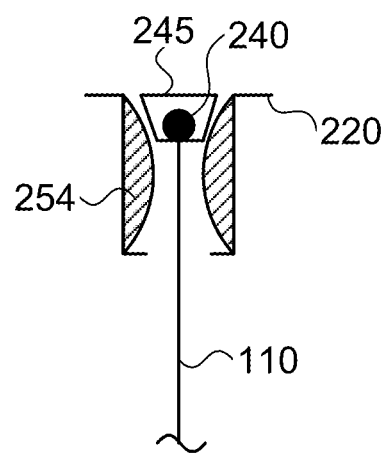

Reference is now made to FIG. 16, showing an alternative embodiment of the shock absorbing mechanism comprising a bottleneck member 254 made of an elastically deformable polymer. Similarly to the embodiment in FIG. 15, the member 250 puled by the cord 110 elastically deforms the bottleneck member 254 such that oscillations in cord tension are quenched.

Figure 17:
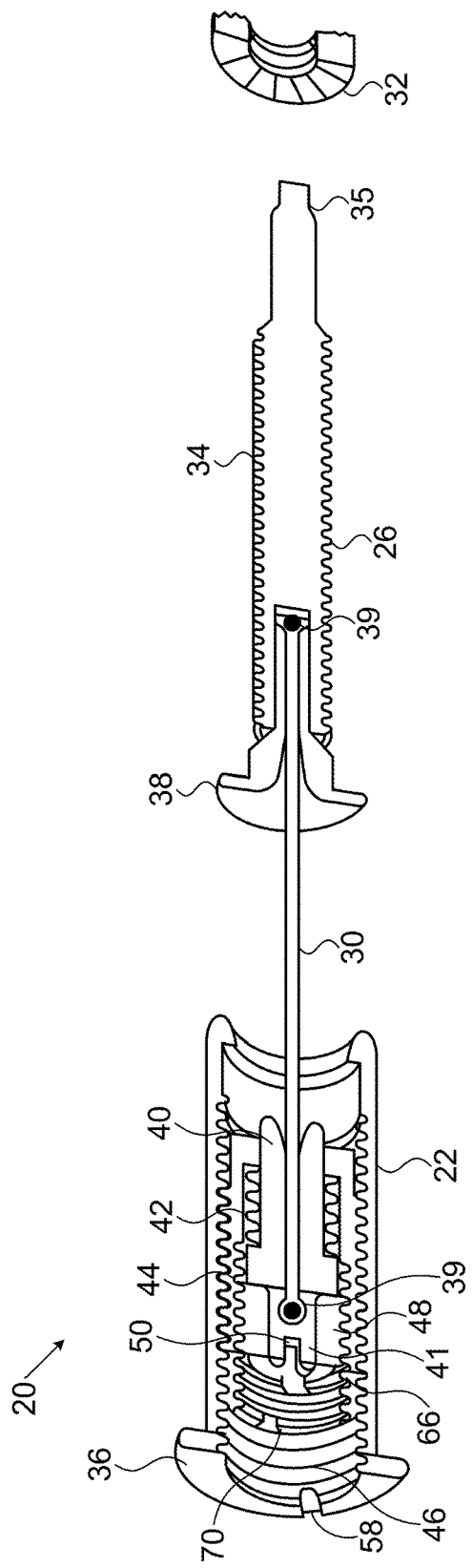
FIG. 17 is a schematic illustration of the device.

Reference is now made to FIG. 17, schematically showing details of device 20, in accordance with an embodiment of the present invention. Anchors 22 and 26 are made from a rigid biocompatible material, such as 316LVM-type stainless steel or titanium alloy, with a cylindrical shape for insertion into cylindrical bores that are drilled in the bones. The diameter of anchor 22 is typically greater than that of anchor 26, for reasons that will be explained below. For example, anchor 22 may be 12 mm long and 6 mm in diameter, while anchor 26 is 11 mm long and 3 min in diameter. Alternatively, other dimensions may be chosen depending, inter alia, on the dimensions and condition of the bones in which the anchors are to be implanted. Anchors 22 and 26 may be coated with a bone growth promoter, such as hydroxyapatite.

Anchor 26 in this embodiment has an external thread 34, which accepts a nut 32 over a distal end 35 of the anchor (i.e., the end that is inserted through the bone) and may also be used to screw anchor 26 into the bone itself. Anchors 22 and 26 have respective collars 36, 38 at their proximal ends, which engage the bone surface when the anchors have been completely inserted into the respective bores. Nut 32 is then fastened onto thread 34 so as to secure anchor 26 firmly in place in the bone. Cord 30 may comprise any flexible (though inelastic), biocompatible material of sufficient strength to withstand the forces exerted by and on the bones of the foot. The cord may comprise either a single strand or multiple strands of a suitable polymer or metal filament. For example, cord 30 may comprise a braided cable made from 316LVM-type stainless steel wire, with an overall diameter of about 0.5 mm. Cord 30 is held inside anchor 22 by a holder 40, with a head 41 attached to its proximal end. Cord 30 may be retained inside holder and collar 38, for example, by means of knots 39 tied at the ends of the cord, or by welding, or by any other suitable means of fastening. In an alternative embodiment (not shown in the figures but considered to be within the scope of the claims), anchors 22 and 26 may be connected by multiple cords, which are configured as a sort of "hammock" between the bones, in order to avoid and relieve local stress points.

Holder 40 also retains and compresses a spring 42. A screw 48 controls the position of holder 40 and thus adjusts the degree of compression and the baseline force on spring 42. Screw 48 has an outer thread, which travels along an inner thread in a wider screw 44. Screw 44 has an outer thread, which travels along a matching internal thread 46 in anchor 22.

Spring 42 controls the tension in cord 30. The spring typically comprises an elastic biocompatible material, such as stainless steel. Alternatively, device 20 may comprise other sorts of mechanically-loaded elements that create mechanical resistance while deforming, such as a flexible polymer or viscoelastic material, a magnetic element applying mechanical force during movement, or a pneumatic or hydraulic element configured to resist geometrical movement.

The compression of spring 42 can be adjusted by rotation of screw 48 (as described in greater detail herein below). Turning screw 48 clockwise (assuming thread 48 to be right-handed) compresses the spring, creating a corresponding "zero-state tension" in cord 30. For example, the zero-state tension may be set to a value in the range between approximately 10 and 15 Newton, although higher and lower values of tension may also be used, depending on clinical conditions.

The longitudinal position of holder 40 within anchor 22 is controlled by an adjustment mechanism comprising screw 44, which travels along internal thread 46 inside the anchor. For example, turning screw 44 counterclockwise (assuming thread 46 to be right-handed) causes holder 40 to shift longitudinally in the proximal direction, thus drawing cord 30 into anchor 22. In this manner, the length of the cord extending between the anchors is reduced, and the intermetatarsal angle is reduced accordingly. Alternatively, screw 44 may be turned clockwise to play out the cord and thus reduce the force exerted between the metatarsal bones.

The adjustment mechanism in device 20 enables the surgeon to precisely, easily and smoothly control the intermetatarsal angle after implantation of the anchors. Adjustment may be achieved simply by turning screw 48, rather than having to manually attempt to tie a suture at the appropriate length as in methods that are known in the art. Furthermore, the configuration of device 20, with screw 48 accessible at the proximal end of anchor 20, makes it possible for the surgeon to readjust the length of cord 30 at a later time if desired. Although the pictured embodiments specifically show a screw-based adjustment mechanism, and this mechanism is advantageous both for initial implantation and subsequent adjustment, other types of mechanisms, such as clips or snaps, may alternatively be used.

Spring 42 serves as a shock absorber, by deforming in response to forces exerted on cord 30. Typically, in the course of walking, metatarsal bones 24 and 28 tend to move cyclically apart and back together, thus exerting a cyclical force on cord 30. In addition, stronger forces may be exerted on the cord when the foot receives a sudden impact, due to jumping or kicking, for example. These forces can fatigue both cord 30 and the bones around anchors 22 and 26, and may lead eventually to failure of device 20 or, what is worse, fractures of the bones. Spring 42 absorbs a part of these forces and thus helps to protect against device failure and bone fracture.

As noted above, the surgeon can adjust the initial tension in spring 42 by means of a force adjuster, in the form of screw 48. Turning this screw causes it to travel longitudinally along an internal thread within screw 44, with which screw 48 is coaxial. This longitudinal motion of screw 48 presses or releases cord holder 40 against spring 42, thus increasing or decreasing the baseline compression of the spring and altering its response to force exerted on cord 30.

In an alternative embodiment (not shown in the figures), the shock absorber in device 20 may comprise two (or more) shock absorbing elements with different responses to the force exerted on cord 30. For example, spring 42 may comprise two parts, in series or in parallel. A first part with a low spring constant absorbs small forces over a certain initial range of movement. Once this range is exceeded, the second part of the spring, with a higher spring constant, absorbs the excess force. This sort of combined shock absorber can enhance patient comfort and reduce the chances of damage to the device and to the bones in which the device is implanted.

To begin the adjustment procedure, a fixed tip 54 of tool 52 is inserted into a central socket 50 of head 41 inside anchor 22. Head 41 is connected to cord holder 40, as noted above. In the pictured embodiment, socket 50 and tip 54 are both square, but other matching shapes may similarly be used. The purpose of socket 50 and tip 54 is to prevent rotation of cord 30 as screws 44 and 48 are turned. Similarly, protrusions 56 at the periphery of tool 52 are fixed and engage recesses 58 in collar 36 to prevent rotation of anchor 22 after it has been implanted in bone 24.

Screws 48 and 44 can be adjusted separately and independently by turning drivers 60 and 62, respectively. The drivers, which are coaxial, are typically controlled by respective knobs or wheels at the proximal end of tool 52 (not shown). Recesses 64 on driver 60 engage protrusions 66 on screw 48, while protrusions 68 on driver 62 engage recesses 70 on screw 44. Thus, in a typical procedure, the surgeon holds tool 52 and tip 54 still, without rotation, while rotating each of drivers 60 and 62 in turn in order to achieve the desired baseline compression of spring 42 and zero-state tension on cord 30, along with the desired length of cord 30 between anchors 22 and 26.

In an alternative embodiment, tool 52 is provided as part of a surgical kit, attached to implant 20. In this embodiment, tip 54 may be attached to socket 50 by various means, such as by laser welding. In order to detach tool 52 from implant 20 after implantation, tip 54 may be weakened, by a groove 55 formed near the proximal end of the tip, for example, to enable the operator to easily disengage tool 52 by breaking off tip 54 at the conclusion of the procedure.

Although tool 52 is shown in the pictured embodiments as a single comprehensive tool, which performs all the functions described above, these functions may alternatively be performed by two or more different tools, which are configured to perform the various adjustment functions separately.

The invention claimed is:

1. An implantable device, comprising:
   (a) a proximal anchor, configured to be implanted inside a first bore in a first metatarsal;
   (b) a distal anchor, configured to be implanted inside and extending at least partially through a drilled channel in a second metatarsal, adjacent to said first metatarsal;
   (c) a cord mechanically interconnecting said proximal and distal anchors;
   (d) at least one shock absorber comprising an elongate housing in the proximal anchor; an elongated tubular cord holder adapted to move longitudinally within the housing, a passage in the cord holder receiving the cord and having a bottleneck adapted to retain the cord, said cord holder being mechanically connected to said housing via a damping member,
   said proximal anchor having a collar larger than the opening in said metatarsal in which said proximal anchor is implanted; said collar preventing said cord to bone contact;
   wherein said cord holder within said housing prevents said cord from contacting cortical surface of the first or second metatarsal.

2. The implantable device according to claim 1, wherein said cord is provided with a shock absorber as an integral portion thereof.

3. The implantable device according to claim 1, wherein said damping member is selected from the group consisting of a spring, a hydraulic piston, a deformable polymer, a deformation energy dampening element, a spring-controlled bellows, spring-controlled telescopic member and any combination thereof.

4. The implantable device according to claim 1, wherein said damping member is configured for operation under compression or extension.

5. The implantable device according to claim 1, wherein the shock absorber comprises an elongate housing threaded into the proximal or distal anchor, and a cord tension force is adjustable due to thread displacement of said shock absorber along said proximal or distal anchor.

6. The implantable device according to claim 1, in which at least one said anchor comprises an intramedullary nail.

7. The implantable device according to claim 1, wherein the distal anchor extends fully through the drilled channel in the second metatarsal.

8. The implantable device according to claim 1, further comprising a male thread on said distal anchor.

9. The implantable device according to claim 1, wherein said cord holder is freely rotatable within said housing to prevent said cord from twist kinking when said housing is rotated.

10. The implantable device according to claim 1, wherein the proximal anchor has a larger diameter than the distal anchor and the distal anchor and the second anchor is configured to pass through the bore in the first bone into the drilled channel inside the second bone.

11. The implantable device according to claim 1, wherein the cord is retained at the distal end of the distal anchor and at the proximal end of the cord holder by respective knots.

12. An implantable device, comprising:
   a first anchor configured to be implanted inside a bore in a first bone;
   a second anchor, configured to be implanted at least partially through a drilled channel inside a second bone;
   a cord extending between the first anchor and the second anchor;
   a shock absorber contained within the bore in at least one of the first and second anchors;
   an elongated tubular cord holder received in the anchor, having a passage for the cord and secured to the cord, and pressing against the shock absorber so that the shock absorber deforms in response to a force exerted on the cord;
   wherein the device is adapted to modify spacing between adjacent bones.

13. The implantable device according to claim 12, wherein the second anchor extends fully through the drilled channel.

14. The implantable device according to claim 12, wherein the second anchor is a cylindrical tube.

15. The implantable device according to claim 12, wherein the cord holder is freely rotatable in said bore, and collars on said first and second anchors prevent cord-to-bone contact when the cord is rotated in said bore.

16. The implantable device according to claim 12, wherein the first anchor has a larger diameter than the second anchor and the second anchor is configured to pass through the bore in the first bone into the drilled channel inside the second bone.

17. The implantable device according to claim 12, wherein the cord is retained at the distal end of the second anchor and at the proximal end of the cord holder by respective knots.

* * * * *